US00PP11870P2

(12) United States Plant Patent
Fruehwirth

(10) Patent No.: US PP11,870 P2
(45) Date of Patent: May 15, 2001

(54) POINSETTIA PLANT NAMED 'ECKABUD'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/431,249

(22) Filed: Nov. 1, 1999

(51) Int. Cl.[7] ..... A01H 5/00

(52) U.S. Cl. ..... Plt./307

(58) Field of Search ..... Plt./307

(56) References Cited

PUBLICATIONS

UPOV–ROM GTITM Computer Database 2000/04, GTI Jouve Retrieval Software, citation for 'Eckabud' Jun. 1999.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Eckabud', characterized by its showy dark red bracts; response time about 9 weeks; dark green leaves; upright and compact plant habit; very freely branching habit; and good postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckabud'.

The new cultivar is a product of a planned breeding program conducted by the Inventor in Encinitas, Calif. The objective of the program is to create new Poinsettia cultivars having interesting bract and leaf display, color and form; strong and freely branching stems; and good post-production longevity.

The new cultivar originated from a cross made by The Inventor of the Poinsettia cultivar '529', disclosed in U.S. Plant Pat. No. 8,371, as the female, or seed parent, with the proprietary selection identified as 587 as the male, or pollen parent.

The cultivar 'Eckabud' was discovered and selected by the Inventor as a flowering plant within the progeny of the cross in a controlled environment in Encinitas, Calif. in December, 1995.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckabud'. These characteristics in combination distinguish 'Eckabud' as a new and distinct cultivar:

1. Showy dark red bracts.
2. Response time about 9 weeks.
3. Dark green leaves.
4. Upright and compact plant habit.
5. Very freely branching habit.
6. Good postproduction longevity.

In side-by-side comparsions conducted in Encinitas, Calif., plants of the new Poinsettia have darker leaves and bracts than plants of the male parent, the selection 587. Compared to plants of the female parent, the cultivar '529', plants of the new Poinsettia are more compact.

Plants of the new Poinsettia can be compared to plants of the cultivar '490', disclosed in U.S. Plant Pat. No. 7825. However, in side-by side comparisons conducted in Encinitas, Calif., plants of the new Poinsettia differed from plants of '490' in the following characteristics:

1. Plants of the new Poinsettia are slightly taller and have a more rounded canopy than plants of '490'.
2. Plants of the new Poinsettia have fewer but slightly broader leaves than plants of '490'.
3. Flower bract color of the new Poinsettia is somewhat brighter red than flower bract color of '490'.
4. Cyathia clusters of the new Poinsettia are more developed than cyathia clusters of '490'.
5. Plants of the new Poinsettia flower later than plants of '490'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Eckabud'.

The photograph at the bottom of the first sheet comprises a top perspective view of a typical plant of 'Eckabud'.

The photograph on the second sheet is a close-up view of typical bracts and leaves of 'Eckabud' (left) and '490' (right). Bract and foliage colors in the photographs may differ from actual colors due to light reflectance.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commerical practice in a glass-covered greenhouse with day temperatures ranging from 21 to 27° C., night temperatures ranging from 18 to 20° C.,and light levels about 4,000 foot-candles. Plants were grown in 16-cm pots, pinched one time, and flowered under naturally lengthening nights during the fall/early winter. In the following description, color references are made to The Royal Horticultural Society Colour Chart except where general terms of ordinary dictionary significance are used.

Botanical classification: *Euphorbia pulcherrima* Willd. 'Eckabud'.

Parentage:

*Female parent.*—*Euphorbia pulcherrima* Willd. '529', disclosed in U.S. Plant Pat. No. 8,371.

*Male parent.*—Proprietary selection of *Euphorbia pulcherrima* Willd. identified as 587.

Propagation:

*Type cutting.*—Terminal cuttings.

*Time to initiate roots.*—Summer: About 7 days at 24° C. Winter: About 10 days at 22° C.

*Time to develop roots.*—Summer: About 26 days at 24° C. Winter: About 26 days at 22° C.

*Rooting habit.*—Freely branching, becoming fibrous with development.

Plant description:

*Plant form.*—Inverted triangle; canopy rounded.

*Growth habit.*—Upright. Very freely branching. Branching is enhanced by removing the shoot apex.

*Plant vigor.*—Moderate.

*Plant height.*—About 28 cm.

*Crop time.*—From unrooted cuttings to a flowering plant in a 16-cm container, about 17 weeks are required.

*Stem description.*—Number of lateral branches: About nine lateral branches are formed after removal of the terminal apex. Lateral branch length: About 18 cm. Internode length: About 1 cm. Stem color: 146A to 146B.

*Foliage description.*—Quantity of leaves per lateral branch: About 8. Length: About 12 cm. Width: About 8.75 cm. Shape: Mostly ovate, occasionally lobed. Apex: Acuminate. Base: Rounded acute. Margin: Entire. Texture: Smooth, dull; very sparse pubescence on lower surface. Aspect: Somewhat concave, folded at midrib. Color: Young foliage, upper surface: Darker than 147A. Young foliage, lower surface: 147B. Mature foliage, upper surface: Darker than 147A. Mature foliage, lower surface: 147B. Venation, upper surface: 147C. Venation, lower surface: 147B. Petiole: Length: About 4.5 cm. Diameter: About 2 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long conditions. Response time is about 9 weeks.

*Quantity of inflorescences.*—One per lateral branch, usually about nine per plant.

*Inflorescence size including bracts.*—Diameter: About 31 cm. Height (depth): About 5 cm.

*Flower bracts.*—Quantity of flower bracts per inflorescence: Usually about 12 primary bracts and about 6 to 10 smaller secondary bracts per inflorescence. Length, largest bracts: About 15 cm. Width, largest bracts: About 10 cm. Shape: Mostly ovate, occasionally lobed. Apex: Acuminate. Base: Rounded acute. Margin: Entire. Texture: Smooth. Aspect: Held slightly upright; somewhat concave, folded at midrib. Color: Developing, upper surface: More crimson than 46A. Developing, lower surface: 46B. Mature, upper surface: Brighter than 45A. Mature, lower surface: Not as gray as 53C.

*Cyathia.*—Quantity: Usually about 10 per corymb. Diameter of cyathia cluster: About 2 by 2 cm. Length: About 9 mm. Width: About 5 mm. Color: Immature: 144A. Mature: 144A. Peduncle: Length: About 3 mm. Aspect: Strong, erect. Color: 144B. Stamens: Stamen number: Ten to twelve true stamen with numerous stamenodes per cyathium. Anther length: About 1 mm. Anther shape: Oval. Anther color: 45A. Amount of pollen: Scarce. Pollen color: 7A. Pistils: No pistillate flowers observed. Nectary color: 2A.

Disease resistance: Plants of the new Poinsettia have not been observed to be resistant to pathogens common to Poinsettias.

Postproduction longevity: Good; generally plants maintain good substance and bract color for about six to eight weeks under interior conditions.

It is claimed:

1. A new and distinct cultivar of Poinsettia plant named 'Eckabud', as illustrated and described.

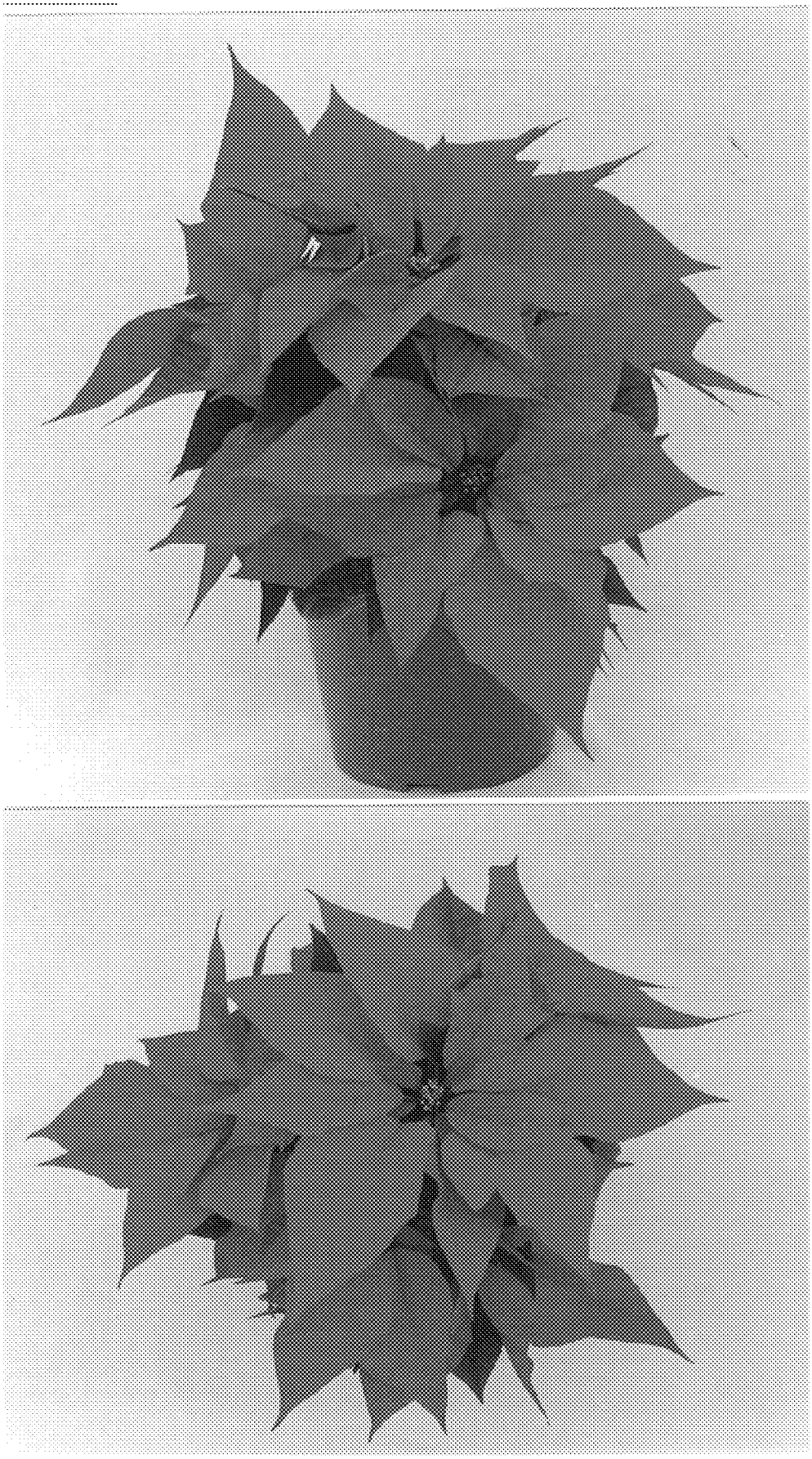

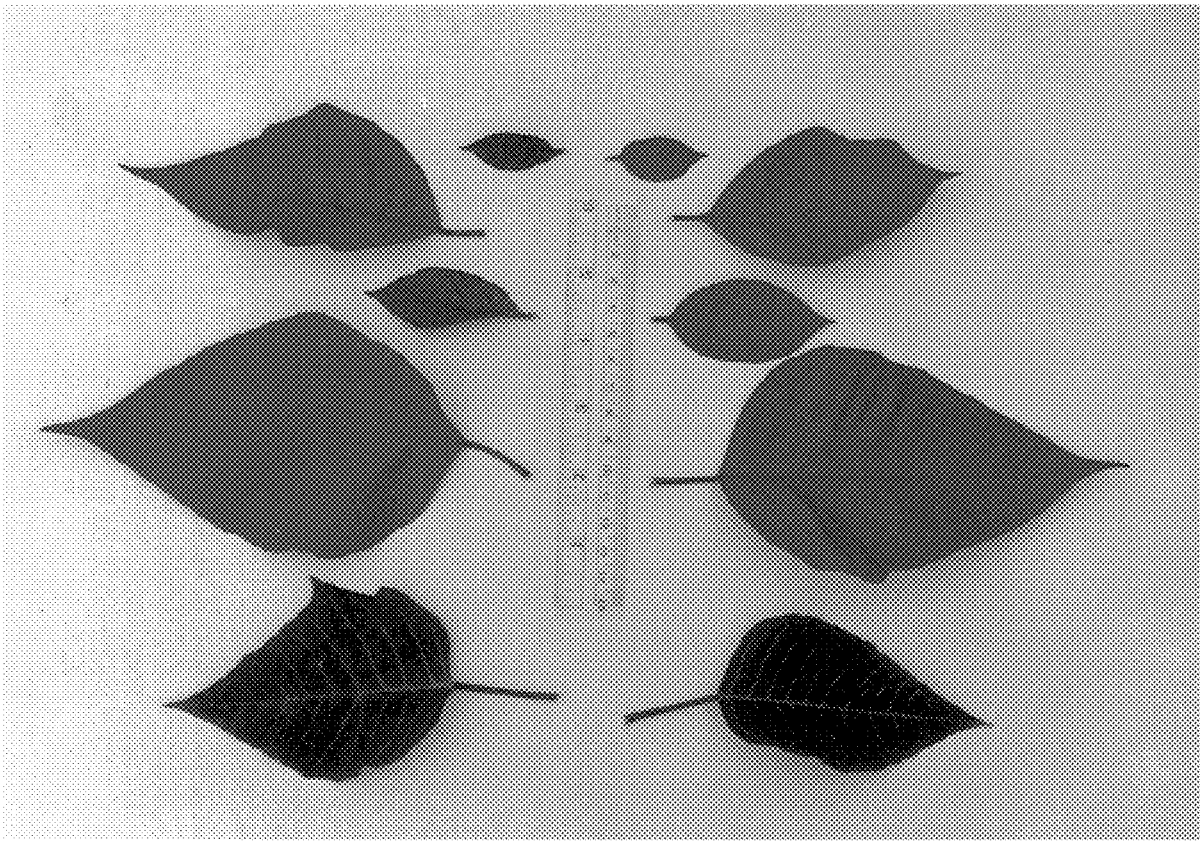

* * * * *